United States Patent [19]

Devic

[11] Patent Number: 4,966,984
[45] Date of Patent: Oct. 30, 1990

[54] PROCESS FOR THE CYCLIZATION OF ORTHOBENZOYLBENZOIC ACID

[75] Inventor: Michel Devic, Sainte Foy les Lyon, France

[73] Assignee: Atochem, France

[21] Appl. No.: 433,365

[22] Filed: Nov. 8, 1989

Related U.S. Application Data

[63] Continuation of Ser. No. 605,817, May 11, 1984.

[30] Foreign Application Priority Data

May 3, 1983 [FR] France .................................. 83 07319
Jul. 5, 1983 [FR] France .................................. 83 11150

[51] Int. Cl.$^5$ .............................................. C07C 50/18
[52] U.S. Cl. .................................................... 552/208
[58] Field of Search ......................................... 552/208

[56] References Cited

U.S. PATENT DOCUMENTS 4,045,456 8/1977 Merger et al. ...................... 552/208

FOREIGN PATENT DOCUMENTS 0100048 8/1975 Japan ................................... 552/208

*Primary Examiner*—Richard L. Raymond
*Assistant Examiner*—Raymond Covington
*Attorney, Agent, or Firm*—Sigalos, Levine & Montgomery

[57] ABSTRACT

The process for the cyclization of orthobenzoylbenzoic acid into anthraquinone comprising heating orthobenzoylbenzoic acid in the solid phase at a temperature between about 300° C. to 400° C. in the presence of a superactive bleaching earth. The invention also comprises a process for the separation of phthalic acid and any phthalic anhydride impurities from orthobenzoylbenzoic acid prior to its cyclization into anthraquinone through the use of said earth at a temperature from 200° C. to 250° C.

6 Claims, No Drawings

PROCESS FOR THE CYCLIZATION OF ORTHOBENZOYLBENZOIC ACID

This application is a continuation of application Ser. No. 605,817, filed May 11, 1984.

BACKGROUND OF THE INVENTION

The present invention concerns a process for the cyclization of orthobenzoylbenzoic acid (OBB acid) in the presence of superactive bleaching earth in order to produce anthraquinone.

It is known to form anthraquinone from OBB acid by heating this acid compound in the presence of concentrated sulfuric acid or an oleum. Such a method is, for instance, reported by Arthur I. VOGEL in "Practical Organic Chemistry", 3rd edition, page 740. The sulfuric acid plays the role of catalyst and solvent for the reaction.

The concentrated sulfuric acid can be replaced by concentrated phosphoric acid or by phosphorus pentoxide. In each of the methods cited above, the large quantity of reagent utilized decreases the efficiency of the corresponding process and creates important pollution problems due to the discarded acid material.

Japanese Patent Application No. 49.7260/74 proposes working with a lesser amount of sulfuric acid, but the operation must then take place in a vacuum and at an elevated temperature above 300° C. This causes operating risks and a high cost for the equipment due to corrosion inherent in the conditions of implementation of such a process. In addition, the recovery by sublimation of the anthraquinone formed can take place only after neutralization of the sulfuric acid with sodium carbonate.

U.S. Pat. No. 2,842,562 also describes a process utilizing a reduced quantity of sulfuric acid. The ring closure (cyclization) of OBB acid takes place at 260° C. in the presence of a third solvent such as trichlorobenzene, with the water formed during the reaction being eliminated by distillation in the form of an azeotropic mixture with the third solvent. The use of the latter solvent complicates the equipment and is uneconomical since the anthraquinone must be recovered by separation from the solvent by steam distillation.

U.S. Pat. No. 2,174,118 proposes hydrofluoric acid as a cyclization catalyst for OBB acid. The use of such a reactant involves major drawbacks due to its very nature; namely, corrosion by the water/hydrofluoric acid combination formed during the course of the operation, difficult recovery of the hydrofluoric acid by dehydration of this same combination, and finally the necessity of operating the ring closure of the OBB acid under pressure.

U.S. Pat. No. 4,304,727 describes a process in which a perfluorinated resin in suspension in an inert organic solvent is used as a cyclization catalyst. Although the recovery of the catalyst is thus facilitated, the OBB acid conversion and the anthraquinone yield are low, for example, equal respectively to 60% and 78%. Additionally, it is necessary to proceed with the separation of the organic solvent from the anthraquinone.

The Japanese Patent Application No. 49.6240/74 recommends cyclizing the OBB acid by heating at 360° C. in the presence of activated clay. This method presents drawbacks rendering it commercially unfeasible due to the necessity of operating in a vacuum, slow ring closure rate, necessity of an intimate mixture of the OBB acid and of the activated clay, and a low practical yield following the absorption by the activated clay of nearly one quarter of the anthraquinone formed. The recovery of the anthraquinone thus absorbed would require costly extraction operations from the clay with an organic solvent and then evaporation of the solvent.

French Utility Certificate No. 76.18956, published under No. 2,314,913, describes the cyclization of OBB acid in the presence of oxygenated compounds of aluminum and silicon, preferably by heating the OBB acid with aluminum silicate in powder form. When the process is conducted in suspension in an organic solvent, the elimination of the solvent and then of the catalyst is complicated and costly whether it is carried out in a fixed bed or in a fluidized bed. In the first case one risks a rapid clogging of the catalyst, while in the second case one risks coming up against a delicate separation of the fine particles of catalyst from the anthraquinone. The best yields of cyclization are also achieved when the latter process is carried out in a vacuum.

SUMMARY OF THE INVENTION

The present invention overcomes the drawbacks of the known processes.

Briefly stated, the present invention comprises the cyclization of OBB acid into anthraquinone comprising heating said acid at a temperature between about 300° C. and 400° C. at atmospheric pressure, in the presence of a superactive bleaching earth. The invention also comprises the process for removal of phthalic acid from OBB acid prior to cyclization of the OBB acid as described below.

DETAILED DESCRIPTION

Superactive bleaching earths is the term currently given to clays of the bentonite type which have been subjected in the known manner to the reaction of a mineral acid, washed with water such that the acid content thereof, expressed as hydrochloric acid, does not exceed 0.1%, and finally dried at a temperature no higher than about 120° C. They are ordinarily used in industry for the bleaching treatment and the purification of oils and fats.

The process according to the invention makes it possible to operate the cyclization of OBB acid without it being necessary to proceed with an intimate mixture of this compound with the superactive bleaching earth.

An operation duration generally between 5 and 120 minutes, most often between 5 and 60 minutes, suffices in order that the ring closure yield is equal to or greater than 90%.

As to temperature, a temperature above 400° C. accelerates the velocity of ring closure of the OBB acid, but causes the formation of an excessive quantity of benzophenone. A temperature below 300° C. requires a too long reaction duration and thus is not economically feasible.

The quantity of superactive bleaching earth is most often between 0.5 and 5 parts by weight; preferably between 1 and 3 parts by weight per part of OBB acid.

Among the superactive bleaching earths suitable for the embodiment of the invention, those which are preferred have a composition by weight contained within the following limits:

$SiO_2$ 70% to 75%, $Al_2O_3$ 10% to 20%, $Fe_2O_3$ 3% to 5%, $MgO$ 1% to 3%, $CaO$ 0.5% to 2%, and materials which can be eliminated by calcination 5% to 10%.

The pH of an aqueous suspension containing 10% superactive bleaching earth of this nature is around 4. The specific surface of such compounds, which exist in the form of particles with dimensions most often smaller than 150 μm, is between about 150 m²/g and 200 m²/g.

It is for instance possible to use a superactive bleaching earth commercially sold under the brand name of "TONSIL" by the SUD-CHEMIE A. G. Company.

It is possible to implement the process of the invention by simply arranging a layer of superactive bleaching earth on a layer of OBB acid. The thickness of the layer of superactive bleaching earth must be such that a rapid diffusion of the anthraquinone formed during heating is permitted. The anthraquinone which separates from the reaction medium by sublimation can be collected by condensation according to any known techniques. One can, for instance, collect the anthraquinone on a surface whose temperature is between 100° C. and 150° C. so as to avoid the condensation of water and volatile organic impurities. The anthraquinone collected thus has a high degree of purity.

The process according to the invention can be carried out in a batch or continuous manner. An example of a continuous embodiment consists in depositing at one end of a stainless steel conveyor belt, moving horizontally at constant velocity, a layer of OBB acid made from molten OBB acid, and depositing on this layer a layer of the superactive bleaching earth, with the conveyor belt then continuing along its path during which time the two superimposed layers are raised to a temperature between 300° C. and 400° C. and the anthraquinone being formed sublimates and condenses, for instance, on the surface of a secondary conveyor belt kept at a temperature between 100° C. and 150° C. and moving above the principal conveyor belt and parallel to same. The used superactive bleaching earth is evacuated at the end of the principal conveyor belt opposite to the one on which the OBB acid is deposited and can undergo a regeneration treatment for the purpose of its recycling in the process.

OBB acid generally contains phthalic acid and phthalic anhydride as impurities when, as is the case most frequently in industry, it is prepared by the condensation of phthalic anhydride and benzene according to, for instance, the process described in French Patent No. 2,496,097. The concentration of phthalic acid or phthalic anhydride can reach 10% by weight.

Thus, a second object of the invention is a process for the separation of phthalic acid and phthalic anhydride from OBB acid either prior to the cyclization of the OBB acid or separately therefrom.

This process consists of cyclizing the phthalic acid contained in the OBB acid into phthalic anhydride which then separates from the reaction medium by sublimation along with the phthalic anhydride, if any, initially present in the OBB acid, in the presence of a superactive bleaching earth such as described for the cyclization of OBB acid, during the course of a heating stage at a temperature; preferably between 200° C. and 250° C., taking place during the temperature rise in view of the subsequent cyclization of OBB acid in the presence of the same superactive bleaching earth.

The duration of the cyclization operation of the phthalic acid is most often between 1 and 30 minutes.

The other characteristics of the operation, such as for instance, the quantity of superactive bleaching earth, are those dictated by the process utilized for the cyclization of OBB acid.

The separation, in the process of the cyclization of OBB acid, of phthalic acid in the form of phthalic anhydride and of the phthalic anhydride, if any, initially present in the OBB acid, is economical and of certain industrial interest. The pre-existing phthalic anhydride and/or the phthalic anhydride formed from phthalic acid can, in fact, be advantageously recycled into the process of the synthesis of OBB acid, after having been recovered for instance by condensation according to any known technique such as the condensation on a surface whose temperature is selected between 20° C. and 100° C.

The process according to the invention can be carried out in a batch or continuous manner.

An example of continuous embodiment consists of utilizing, in the method of continuous cyclization of OBB acid on a conveyor belt described above, an OBB acid containing phthalic acid and phthalic anhydride, if any, and a layer of the superactive bleaching earth, subjecting the two superimposed layers to heating at a temperature between 200° C. and 250° C. during the course of travel of the belt to cyclize the phthalic acid into phthalic anhydride, and that the phthalic anhydride thus formed sublimes together with the phthalic anhydride, if any, already present in the OBB acid in order to be collected on the surface of a conveyor belt arranged above the principal belt.

The invention will be further described in connection with the following examples which are set forth for purposes of illustration only.

EXAMPLE 1

2.70 g of OBB acid in powder form are mixed coarsely in the cold state with 6.30 g of "TONSIL" of reference BW3. This mixture is deposited in the form of a layer of practically uniform thickness of 0.5 cm on the horizontal bottom of a cylindrical stainless steel container having a diameter of 80 mm and a height of 15 mm. It is covered with a fine stainless steel gauze. A stainless steel cover is placed on the container which is then raised to 400° C. by immersion in a molten metal bath and kept at that temperature for 6 minutes. . The temperature of the cover is about 100° C. during this operation.

After removal of the container from the heating bath and cooling, 2.31 g of anthraquinone are collected on the cover and on the gauze, making it possible to collect crystals of anthraquinone which can detach themselves from the cover. These 2.31 g of anthraquinone represent a 93.0% yield of cyclization of the OBB acid.

EXAMPLE 2

By operating as in Example 1, but at a temperature of 300° C. for 1 hour, 2.26 g of anthraquinone are collected, representing a cyclization yield of the OBB acid of 90.8%.

EXAMPLE 3

By proceeding as in Example 1, but with 4.5 g of OBB acid and 4.5 g of the same superactive bleaching earth, 3.77 g of anthraquinone are obtained, representing a cyclization yield of the OBB acid of 91.0%.

EXAMPLE 4

In the container of Example 1, a layer of 2.70 g of molten OBB acid is deposited which is allowed to cool and solidify at ambient temperature prior to depositing on it a layer of practically uniform thickness of 6.5 g of the same bleaching earth as in Example 1.

By then proceeding as in Example 1, 2.35 g of anthraquinone are collected representing a 94.7% yield of cyclization of the OBB acid.

EXAMPLE 5

2.7 g of a product containing 90% by weight of OBB acid and 10% by weight of phthalic acid are deposited in the molten state on the bottom of a cylindrical stainless steel container having a diameter of 80 mm and a height of 15 mm. After cooling and solidification of the layer thus obtained, one arranges on it a layer of practically uniform thickness of 6.3 g of superactive bleaching earth commercially sold by the SUDCHEMIE A. G. Company under the brand name of "TONSIL", reference BW3.

The container is covered with a stainless steel lid and is heated to 250° C. by immersion in a bath of molten metal and kept at this temperature for 6 minutes. The temperature of the cover is about 90° C. during this period; at the end of which the cover is removed and replaced by another one which will serve to collect the anthraquinone which will then form by cyclization of the OBB acid under the conditions described in this application.

On the cover removed following the stage at 250° C., 0.18 g of a sublimate are collected, whose analysis by thin layer chromatography shows that it contains practically only phthalic anhydride.

EXAMPLE 6
(COMPARATIVE)

By proceeding as in Example 5, but in the absence of superactive bleaching earth, only 74% of the phthalic anhydride recovered in Example 5 is collected.

EXAMPLE 7

By proceeding as in Example 5, but with a product containing by weight 80% OBB acid, 10% phthalic acid and 10% phthalic anhydride, 0.44 g of sublimate are obtained, containing practically only phthalic anhydride.

EXAMPLE 8
(COMPARATIVE)

By proceeding as in Example 7, but in the absence of superactive bleaching earth, only 61% of the phthalic anhydride recovered in Example 7 is obtained.

EXAMPLE 9

By proceeding as in Example 5, but with a product containing by weight 90% OBB acid, 5% phthalic acid, 5% phthalic anhydride, and a heating process at 250° C. for a duration of 12 minutes, one recovers 0.253 g of a sublimate which contains practically only phthalic anhydride.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A process for the cyclization of orthobenzoylbenzoic acid to anthraquinone comprising first mixing or layering solid orthobenzoylbenzoic acid and a solid superactive bleaching earth, said mixture or layer being of a thickness such that anthraquinone formed and sublimated diffuses totally therefrom, heating said mixture of solids or layer of solids without agitation at atmospheric pressure and at a temperature between about 300° C. and 400° C.; said solid superactive bleaching earth being a clay of the bentonite type which has been subjected to the reaction of a mineral acid, washed with water such that the acid content thereof, expressed as hydrochloric acid, does not exceed 0.1%, for about 5 to 120 minutes to cyclize substantially all of said acid to anthraquinone.

2. The process of claim 1 wherein said superactive bleaching earth contains, in percent by weight:

$SiO_2$: 70 to 75%,
$Al_2O_3$: 10 to 20%,
$Fe_2O_3$: 3 to 5%,
MgO: 1 to 3%,
CaO: 0.5 to 2%, and
Materials eliminated by calcination: 5 to 10%, and said earth has a specific surface between about 150 $m^2/g$ and 200 $m^2/g$ and is formed of fine particles having dimensions of less than 150 $\mu m$.

3. The process of claim 1 or 2 wherein said solid and said solid earth are layered, with a layer of said solid earth on said solid acid, in such a thickness that the anthraquinone being formed and subliminated diffuses totally therefrom.

4. The process of claim 1 or 2 wherein the quantity of said earth used is from about 0.5 to 5 parts by weight for each part by weight of said acid and the reaction time is from about 5 to 60 minutes.

5. The process of claim 1 wherein prior to cyclization of said orthobenzoylbenzoic acid, said acid is treated to remove any phthalic acid contained therein, said treatment comprising heating the orthobenzoylbenzoic acid, in the solid phase and at atmospheric pressure, at a temperature between about 200° C. to 250° C. in the presence of 0.5 to 5 parts by weight for each part by weight of the orthobenzoylbenzoic acid of a solid superactive bleaching earth for a time sufficient to cyclize said phthalic acid to phthalic anhydride and removing said anhydride.

6. The process of claim 5 wherein the reaction time for cyclization of said phthalic acid is from about 1 to 30 minutes at 200° C. to 250° C. and said reaction takes place during the time the temperature is being raised to between about 300° C. to 400° C. to cyclize said orthobenzoylbenzoic acid.

* * * * *

UNITED STATES PATENT AND TRADEMARK OFFICE
CERTIFICATE OF CORRECTION

PATENT NO. :  4,966,984
DATED      :  October 30, 1990
INVENTOR(S):  Michel Devic It is certified that error appears in the above-identified patent and that said Letters Patent is hereby corrected as shown below:

ON TITLE PAGE:    item [63], delete "May 11" and insert therefore -- May 1 --.

Signed and Sealed this

Twenty-eighth Day of April, 1992

Attest:

HARRY F. MANBECK, JR.

Attesting Officer    Commissioner of Patents and Trademarks